United States Patent [19]
Sievert et al.

[11] Patent Number: 6,143,938
[45] Date of Patent: Nov. 7, 2000

[54] PROCESS FOR PERHALOCYCLOALKANE PURIFICATION

[75] Inventors: Allen Capron Sievert, Elkton, Md.; V. N. Mallikarjuna Rao, Wilmington, Del.

[73] Assignee: E. I. du Pont de Nemours and Company, Wilmington, Del.

[21] Appl. No.: 09/429,271

[22] Filed: Oct. 29, 1999

Related U.S. Application Data

[60] Provisional application No. 60/107,818, Nov. 10, 1998.

[51] Int. Cl.[7] .................................................. C07C 17/38
[52] U.S. Cl. ............................................................ 570/177
[58] Field of Search ...................................... 570/177, 169

[56] References Cited

U.S. PATENT DOCUMENTS

| | | | |
|---|---|---|---|
| 5,001,287 | 3/1991 | Fernandez et al. | 570/178 |
| 5,105,035 | 4/1992 | Wang et al. | 570/177 |
| 5,569,797 | 10/1996 | Fu et al. | 570/177 |
| 5,705,718 | 1/1998 | Cheminal et al. | 570/177 |
| 5,780,695 | 7/1998 | Kalnes | 570/177 |
| 5,856,595 | 1/1999 | Merkel et al. | 570/177 |

FOREIGN PATENT DOCUMENTS 2 318 350   4/1998   United Kingdom .

Primary Examiner—Alan Siegel

[57] ABSTRACT

A process is disclosed for recovering at least one perhalocycloalkane selected from the group consisting of octafluorocyclobutane, hexafluoro-bis(trifluoromethyl) cyclobutane (1,2 and 1,3; cis and trans), 1,2-dichloro-1,2,3,3,4,4-hexafluorocyclobutane (cis and trans), 1,1,2,2-tetrachloro-3,3,4,4-tetrafluorocyclobutane, 1-chloro-1,2,2,3,3,4-hexafluoro-4-(trifluoromethyl)-cyclobutane, heptafluoro(trifluoromethyl)cyclobutane and chloroheptafluoro-cyclobutane from a mixture comprising (a) the perhalocycloalkane, (b) olefinic impurity and optionally (c) saturated fluorine-containing impurity selected from the group consisting of hydrochlorofluorocarbons, hydrofluorocarbons and mixtures thereof. The process involves (1) contacting the mixture with chlorine under conditions suitable for chlorinating the olefinic impurity, thereby converting the olefinic impurity to a saturated impurity containing at least one chlorine substituent and reducing the hydrogen content of the saturated fluorine-containing impurity (if present), and (2) separating said at least one perhalocycloalkane from the products produced during the chlorination of (1).

Also disclosed is a process for producing n-decafluorobutane. The process involves contacting a mixture comprising octafluorocyclobutane (i.e., C-318) and 1,1,1,2,3,4,4,4-octafluorobutene-2 (FC-1318my) with chlorine under conditions suitable for converting the FC-1318my to 2,3-dichloro-1,1,1,2,3,4,4,4-octa-fluorobutane (i.e., CFC-318mbb); separating the C-318 from the CFC-318mbb; and reacting the CFC-318mbb with HF.

7 Claims, No Drawings

PROCESS FOR PERHALOCYCLOALKANE PURIFICATION

This application claims the priority benefit of U.S. Provisional Application Ser. No. 60/107,818, filed Nov. 10, 1998.

FIELD OF THE INVENTION

The present invention relates to a process for the purification of halofluorocarbons, more particularly, to the purification of perhalocycloalkanes containing fluorine by the removal of olefinic and/or hydrogen-containing fluorocarbons.

BACKGROUND OF THE INVENTION

Perfluorocyclobutane (C-318, b.p. −6° C.) is a valuable material which can be used as a propellant, etch gas, and fire extinguishant. This compound is typically made by cyclodimerization of tetrafluoroethene (TFE) or is recovered as a by-product from the manufacture of TFE. As a result C-318 may be contaminated with unsaturates such as E- and Z-perfluoro-2-butene (i.e., $CF_3CF=CFCF_3$ or FC-1318my) and perfluoroisobutene (i.e., $(CF_3)_2C=CF_2$ or PFIB or FC-1318mmt). These compounds, especially the latter, are highly toxic and must be removed prior to commercial use. FC-1318's are difficult to separate from C-318 by distillation as the boiling points are similar.

Perfluorobutane which can be used as an etch gas has typically been prepared by cumbersome methods. One such preparation disclosed by J. Burdon et al., J. Fluorine Chem., 40 (1988) 283–318 involves the fluorination of butane by cobalt trifluoride to yield at least 51 compounds, among which perfluorobutane was identified.

U.S. Pat. No. 5,001,287 discloses a process for treating an impure mixture consisting essentially of at least one olefinic impurity and at least one saturated halocarbon by contacting the mixture with a source of hydrogen in the presence of a hydrogenation catalyst. The saturated halocarbon includes perfluorocyclobutane and the catalyst includes Group VIII metals.

There is a need for alternative methods of purification.

SUMMARY OF THE INVENTION

This invention provides a process for recovering at least one perhalocycloalkane selected from the group consisting of octafluorocyclobutane, hexafluoro-bis(trifluoromethyl)cyclobutane (1,2 and 1,3; cis and trans), 1,2-dichloro-1,2,3,3,4,4-hexafluorocyclobutane (cis and trans), 1,1,2,2-tetrachloro-3,3,4,4-tetrafluorocyclobutane, 1-chloro-1,2,2,3,3,4-hexafluoro-4-(trifluoromethyl)-cyclobutane, heptafluoro(trifluoromethyl)cyclobutane and chloroheptafluorocyclobutane from a mixture comprising (a) said at least one perhalocycloalkane and (b) olefinic impurity (i.e., one or more olefinic compounds). The process comprises (1) contacting the mixture with chlorine under conditions suitable for chlorinating the olefinic impurity, thereby converting the olefinic impurity to a saturated impurity containing at least one chlorine substituent and (2) separating said at least one perhalocycloalkane from the saturated chlorine-containing impurity produced from the olefinic impurity in (1).

Also provided is a process for producing n-decafluorobutane (i.e., $CF_3CF_2CF_2CF_3$ or FC-31-10) which comprises contacting a mixture comprising octafluorocyclobutane (i.e., C-318) and 1,1,1,2,3,4,4,4-octafluorobutene-2 (i.e., $CF_3CF=CFCF_3$ or FC-1318my) with chlorine under conditions suitable for converting the FC-1318my to 2,3-dichloro-1,1,1,2,3,4,4,4-octafluorobutane (i.e., $CF_3CClFCClFCF_3$ or CFC-318mbb); separating the C-318 from the CFC-318mbb; and reacting the CFC-318mbb with HF.

DETAILS OF THE INVENTION

In one embodiment, the invention process is conducted by contacting either batchwise, or continuously, an impure mixture consisting essentially of olefinic impurity and at least one perhalocycloalkane selected from the group consisting of octafluorocyclobutane, hexafluorobis(trifluoromethyl)cyclobutane (1,2 and 1,3; cis and trans), 1,2-dichloro-1,2,3,3,4,4-hexafluorocyclobutane (cis and trans), 1,1,2,2-tetrachloro-3,3,4,4-tetrafluorocyclobutane, 1-chloro-1,2,2,3,3,4-hexafluoro-4-(trifluoromethyl)cyclobutane, heptafluoro-(trifluoromethyl)cyclobutane and chloroheptafluorocyclobutane, with chlorine in the presence of a chlorination catalyst.

The fluorine-containing perhalocycloalkanes recovered in accordance with this invention are known compounds in the art. For example, octafluorocyclobutane is typically produced during the manufacture of tetrafluoroethylene and hexafluoropropylene by the pyrolysis of chlorodifluoromethane as discussed in U.S. Pat. No. 5,672,784. Octafluorocyclobutane can also be produced by the electrolysis of 1,1,2,2-tetrafluorocyclobutane as disclosed in European Patent Application. No. 455,399. During the electrolysis process, the major product (about 62 mole %) is octafluorocyclobutane. However, minor amounts (about 7 mole %) of product with an intermediate degree of fluorination are also found.

Representative olefins which can be removed from the perhalocyclobutane by the process of this invention include $CF_2=CF_2$, $CClF=CF_2$, $CF_3CF=CF_2$, $CClF_2CF=CF_2$, cyclo-$C_4F_6$, 1,2-dichloro-3,3,4,4-tetrafluorocyclobutene, $CF_3CF=CFCF_3$, $CF_3CCl=CHCF_3$, $CF_3CCl=CClCF_3$, $(CF_3)_2C=CF_2$ and $CF_2=CFCF_2CF_3$. The chlorine treatment can also remove other unsaturates such as perfluoro-2-butyne.

The mixture which is contacted with chlorine may also comprise saturated fluorine-containing impurities selected from the group consisting of hydrochlorofluorocarbons, hydrofluorocarbons and mixtures thereof, and the process may be run under conditions suitable for chlorinating these saturated impurities as well, thereby reducing the hydrogen content of these compounds (e.g., by forming chlorofluorocarbons). The hydrogen-depleted saturated fluorine-containing impurity produced by this chlorination can also be separated from the perhalocycloalkane(s). Representative saturated impurities which can be removed from the perhalocyclobutane by the process of this invention include $C_2HClF_4$, $C_3HClF_6$, $C_4HClF_8$, $C_4H_2F_8$, penta-, hexa- and heptafluorocyclobutane.

The chlorination catalyst is selected from the group consisting of carbon, fluorided alumina and aluminum fluoride. The carbon catalyst includes activated carbon and acid-washed carbons (e.g., carbons which have been treated with hydrochloric acid or hydrochloric acid followed by hydrofluoric acid). Suitable acid treatment of carbons is described in U.S. Pat. No. 5,136,113. The carbon catalyst also includes three dimensional matrix porous carbonaceous materials. Examples are those described in U.S. Pat. No. 4,978,649. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

By aluminum fluoride is meant at least one of aluminum fluoride (e.g., alpha-$AlF_3$, beta-$AlF_3$, delta-$AlF_3$, eta-$AlF_3$, gamma-$AlF_3$, kappa-$AlF_3$ and/or theta-$AlF_3$). By fluorided alumina is meant a composition comprising aluminum, oxygen and fluorine. The fluoride content of the fluorided alumina can vary over a wide range, from about 0.001% to about 67.8% by weight.

The chlorination of the impurities over the aforementioned catalysts may be carried out at a temperature from about 100° C. to about 450° C., preferably from about 150° C. to about 350° C., and most preferably from about 200° C. to about 300° C. If it is desired to remove hydrogen-containing saturated impurity, then higher temperatures (about 350° C. to about 450° C.) are preferred.

The pressure used in the chlorination is not critical and may be subatmospheric, atmospheric, or superatmospheric. Preferably, the chlorination is done at atmospheric pressure or for convenience in separations later in the process at pressures up to 30 atmospheres.

Contact time over the catalyst may vary from about 1 second to about 200 seconds depending on the type of impurities (olefins versus saturated compounds); a contact time of about 5 seconds to about 60 seconds is generally preferred. Longer contact times are preferred if it is desired to convert all saturated compounds containing hydrogen to chlorinated compounds.

In a second embodiment, the impure mixture containing olefinic impurity is contacted with chlorine, and the impurity is photochlorinated in the vapor or liquid phase; preferably the liquid phase. The photochlorination process of the invention is carried out at temperatures from about −80° C. to about 100° C., especially at temperatures from about −30° C. to about 60° C., where it is possible to operate at subatmospheric, atmospheric or superatmospheric pressures.

The chlorination can be carried out in a solvent, which represents the liquid phase. The pressure and temperature can then be varied over a somewhat wider region than when operating without solvent. Advantageously, solvents are used which boil above the boiling point of the impure perhalocycloalkanes and are inert under the chlorinating conditions, for example, perhalogenated hydrocarbons.

In the process of the invention, the perhalocycloalkane, with or without solvent, is generally placed in an exposure apparatus equipped with a condenser and elementary chlorine is passed into the liquid with exposure to light, where the chlorine dissolves and is extensively reacted. The process is preferably performed in the absence of solvent.

Compared with the gas-phase photochemical chlorination, this arrangement has the advantage that the separation of hydrogen chloride formed is much easier, since the hydrogen chloride evolves as a gas and can largely be separated by distillation.

Examples of suitable radiation sources include metal-vapor lamps, noble gas discharge lamps or sunlight. The only prerequisite is that the light source have a radiation maximum between 250 and 520 nm.

The molar ratio of chlorine:impurity(ies) should be from about 0.75:1 to about 50:1, preferably from about 1.0:1 to about 20:1.

The chlorination of the olefins typically affords products which have higher boiling points than both the starting olefins and the perhalocycloalkane. For example, typically the major olefinic impurities present in perfluorocyclobutane (C-318) are $CF_3CF=CFCF_3$ (FC-1318my) and $(CF_3)_2C=CF_2$ (FC-1318mmt or PFIB). The boiling points of these compounds are, C-318, −6.1° C.; FC-1318my, 0° C.; and PFIB, 7° C. The chlorinated olefin products are $CF_3CClFCClFCF_3$ (CFC-318mbb) and $(CF_3)_2CClCClF_2$ (CFC-3181x) with a boiling point of 63° C. for both compounds. Other unsaturated impurities that may be present in C-318 include $CF_3CF=CF_2$ (FC-1216my), $CF_2=CFCF_2CF_3$ (FC-1318mcy), and $CF_3C\equiv CCF_3$ (1316mt). The boiling points of these compounds are −29° C., 1° C. and −24.6° C., respectively. The chlorinated products from these impurities are $CF_3CClFCClF_2$ (CFC-216ba, $CClF_2CClFCF_2CF_3$ (CFC-3181b) and a mixture of $CF_3CCl=CClCF_3$ (FC-1316mxx) and $CF_3CCl_2CCl_2CF_3$ (CFC-316maa) with boiling points of 34.8° C., 64° C., 67.8° C. and 131° C., respectively.

For impure perhalocyclobutanes the chlorination products are much higher boiling than the starting impurity. Also under the chlorination conditions oligomerization of the olefinic impurities can occur. Since the products are much higher boiling than the starting impurities, chlorination, followed by distillation is an effective method of preparing very pure perhalocyclobutanes.

If desired, CFC-318mbb, obtained by chlorination of the FC-1318my impurity in the C-318, can be contacted with HF in the presence of a vapor phase fluorination catalyst such as $Cr_2O_3$ at a temperature of at least 300° C. to produce decafluoro-n-butane (i.e., $CF_3CF_2CF_2CF_3$ or FC-31-10). CFC-318mbb can also be contacted with HF in the presence of a liquid phase catalyst, such as $SbCl_xF_{5-x}$, where x is between 0 and 2, to produce FC-31-10.

Without further elaboration, it is believed that one skilled in the art can, using the description herein, utilize the present invention to its fullest extent. The following embodiments are to be construed as illustrative, and not as constraining the remainder of the disclosure in any way whatsoever.

EXAMPLES

| Legend | |
|---|---|
| c-318 is perfluorocyclobutane | 318mbb is $CF_3CClFCClFCF_3$ |
| 318 isom is $C_4Cl_2F_8$ | 328 is $C_4HClF_8$ |
| 1318yc is $CF_2=CFCF_2CF_3$ | 1318my is $CF_3CF=CFCF_3$ |
| 31-10 is n-$C_4F_{10}$ | 31-10 (iso) is iso-$C_4F_{10}$ |
| 41-12 is $C_5F_{12}$ | 42-10 is $C_5HF_{10}$ |
| 52-12 is $C_6HClF_{12}$ | PFIB is $(CF_3)_2C=CF_2$ |
| PFMCB is heptafluoro (trifluoromethyl)cyclobutane | |

Chlorination of C-318 Contaminated with FC-1318's

The chlorination reactor consisted of a 5"(12.7 cm)×0.5" (1.3 cm) o.d. section of Hastelloy™ C nickel alloy tubing. The catalyst was loaded into the reactor and held in place by an Inconel™ nickel alloy screen. The reactor, oriented vertically, was placed in a fluidized sand bath at 300° C. and purged with $N_2$. The reactor was cooled to the reaction temperature and a 1:1 mixture of $Cl_2$ and C-318 was passed through the reactor at temperatures of 170–300° C.

For Example 1, the catalyst used was acid-washed carbon (AWC, 10 mL, 3.56 g). For Example 2, the catalyst used was non-acid-washed carbon (NAW, 10 mL, 6×6 mesh, 3.4×3.4 mm), 4.58 g). For Example 3, the reactor was packed with 10 mL (5.07 g) of a three dimensional matrix porous carbon (TDMP).

Results for Examples 1 to 3 are summarized in Tables 2, 3 and 4, respectively. An analysis of the starting material for Examples 1 to 3 is given in Table 1.

GC analyses of portions of the reactor vapor effluent were carried out on a 20'(6.1 m)×0.125"(3.2 mm) steel column packed with 5% Krytox™ 143AC perfluoroether on 60/80 mesh (0.25/0.18 mm) Carbopak BHT. The temperature program was 60° C. initially for 4 minutes, then 8° C./minute ramp to 190° C.

GC-MS were run on a 105 m×0.25 mm id Rtx-1 column (1.0 micron film thickness). The temperature program was −20° C. for 10 minutes, ramp at 10° C./minute to 150° C., and hold for 30 minutes; the helium flow rate through the column was 1.2 mL/min.

TABLE 1

Composition of C-318 Sample Used for Chlorination Studies

| Component | GC Area % |
|---|---|
| C-318 | 93.0768 |
| 31-10 (n-$C_4F_{10}$) | 1.1307 |
| 31-10 (iso) | 0.6410 |
| 1318my (trans) | 3.1195 |
| 1318my (cis) | 0.1987 |
| 1318yc | 0.0887 |
| 41-12 and PFIB[a] | 0.0143 |
| 41-12 ($C_5F_{12}$) | 0.1318 |
| $C_5F_{10}$ | 0.2404 |
| 328 | 0.6416 |
| 42-10 ($C_5HF_{10}$) | 0.0270 |
| 52-12 ($C_6HClF_{12}$) | 0.0218 |
| Others | 0.6314 |

[a]PFIB content was found to be 31 ppmv in the liquid and 20 ppmv in the vapor.

TABLE 2

(Example 1)
Reaction of the C-318 Mixture with Chlorine over AWC

| Temp. | Flow Rates, cc/minute | | GC Area Percent | | | | | | |
|---|---|---|---|---|---|---|---|---|---|
| ° C. | $Cl_2$ | C-318 | C-318 | $C_4F_{10}$ | PFMCB | $C_5F_{12}$ | 328 | 318 mbb | 318 isom |
| 199 | 10 | 10 | 94.8 | 1.5 | 0.08 | 0.02 | 0.2 | 3.1 | 0.07 |
| 168 | 10 | 10 | 95.0 | 1.5 | 0.08 | 0.03 | 0.2 | 3.1 | 0.08 |
| 299 | 10 | 10 | 95.2 | 1.4 | 0.07 | 0.02 | 0.08 | 2.9 | 0.3 |

TABLE 3

(Example 2)
Reaction of the C-318 Mixture with Chlorine over NAW

| Temp. | Flow Rates, cc/minute | | GC Area Percent | | | | | | |
|---|---|---|---|---|---|---|---|---|---|
| ° C. | $Cl_2$ | C-318 | C-318 | $C_4F_{10}$ | PFMCB | $C_5F_{12}$ | 328 | 318 mbb | 318 isom |
| 170 | 5.2 | 10 | 95.4 | 1.4 | 0.09 | 0.03 | 0.2 | 2.6 | 0.06 |
| 200 | 10 | 10 | 95.0 | 1.4 | 0.08 | 0.04 | 0.2 | 3.0 | 0.08 |
| 300 | 10 | 10 | 95.2 | 1.5 | 0.09 | 0.04 | 0.05 | 3.0 | 0.2 |
| 250 | 10 | 20 | 94.5 | 1.6 | 0.1 | 0.06 | 0.2 | 3.3 | 0.1 |
| 250 | 20 | 10 | 94.2 | 1.7 | 0.2 | 0.06 | 0.2 | 3.5 | 0.2 |

TABLE 4

(Example 3)
Reaction of the C-318 Mixture with Chlorine over TDMP

| Temp. | Flow Rates, cc/minute | | GC Area Percent | | | | | | |
|---|---|---|---|---|---|---|---|---|---|
| °C. | $Cl_2$ | C-318 | C-318 | $C_4F_{10}$ | PFMCB | $C_5F_{12}$ | 328 | 318 mbb | 318 isom |
| 170 | 10 | 10 | 95.0 | 1.5 | 0.1 | 0.05 | 0.2 | 3.0 | 0.04 |
| 200 | 10 | 10 | 94.4 | 1.5 | 0.09 | 0.06 | 0.2 | 3.0 | 0.05 |
| 301 | 10 | 10 | 94.3 | 1.6 | 0.2 | 0.07 | 0.2 | 3.1 | 0.1 |

In all the examples only low levels (<0.005 area %) of 1318s were observed in equilibrated reactor effluent.

Example 4

| Legend | |
|---|---|
| 124a is $CHF_2CClF_2$ | 124 is $CHCl_2CF_3$ |
| 114 is $CClF_2CClF_2$ | 114a is $CCl_2FCF_3$ |
| 123 is $CHCl_2CF_3$ | |

The chlorination reactor was the same as the one used in Examples 1–3. The catalyst was fluorided alumina (2.8 g, 4 mL, 12 to 20 mesh (1.68 to 0.84 mm)) prepared as described in U.S. Pat. No. 4,902,838. The molar ratio of $Cl_2$:c-318:124a was about 4:1:0.1.

GC analysis (mole percent) was accomplished using the same set-up as that described in Examples 1 to 3. The results of the chlorination reaction are shown in Table 5.

TABLE 5

| Temp (° C.) | c-318 | 124a | 124 | 1318my | 114 | 114a | 123 | Others[a] |
|---|---|---|---|---|---|---|---|---|
| FEED | 89.5 | 8.8 | 0.2 | 0.2 | 0.9 | 0.1 | 0.0 | 0.4 |
| 300 | 89.4 | 7.5 | 0.6 | 0.1 | 0.5 | 0.1 | 0.4 | 0.9 |
| 325 | 89.3 | 5.4 | 0.9 | 0.0 | 1.3 | 0.3 | 0.7 | 1.2 |
| 350 | 89.2 | 2.5 | 1.1 | 0.0 | 2.6 | 0.9 | 0.9 | 2.0 |

[a]Others include $CHF_2CF_3$, $CClF_2CF_3$, $CCl_2FCClF_2$, $CCl_3CF_3$, $CF_3CClFCClFCF_3$ and $C_2Cl_4$

What is claimed is:

1. A process for recovering at least one perhalocycloalkane selected from the group consisting of octafluorocyclobutane, hexafluorobis(trifluoromethyl)-cyclobutane (1,2 and 1,3; cis and trans), 1,2-dichloro-1,2,3,3,4,4-hexafluorocyclobutane (cis and trans), 1,1,2,2-tetrachloro-3,3,4,4-tetrafluorocyclobutane, 1-chloro-1,2,2,3,3,4-hexafluoro-4-(trifluoromethyl)cyclobutane, heptafluoro-(trifluoromethyl)cyclobutane and chloroheptafluorocyclobutane from a mixture comprising (a) said at least one perhalocycloalkane and (b) olefinic impurity, comprising:
   (1) contacting the mixture with chlorine under conditions suitable for chlorinating the olefinic impurity, thereby converting the olefinic impurity to a saturated impurity containing at least one chlorine substituent; and
   (2) separating said at least one perhalofluorocycloalkane from the saturated chlorine-containing impurity produced from the olefinic impurity in (1).

2. The process of claim 1 wherein the olefinic impurity is chlorinated in the presence of a catalyst.

3. The process of claim 1 wherein the olefinic impurity is photo-chlorinated.

4. The process of claim 1 wherein the mixture comprises perfluorocyclobutane, $CF_3CF=CFCF_3$ and $(CF_3)_2C=CF_2$, and wherein in (1) $CF_3CClFCClFCF_3$ and $(CF_3)_2CClCClF_2$ are produced.

5. A process for recovering at least one perhalocycloalkane selected from the group consisting of octafluorocyclobutane, hexafluorobis(trifluoromethyl)-cyclobutane (1,2 and 1,3; cis and trans), 1,2-dichloro-1,2,3,3,4,4-hexafluorocyclobutane (cis and trans), 1,1,2,2-tetrachloro-3,3,4,4-tetrafluorocyclobutane, 1-chloro-1,2,2,3,3,4-hexafluoro-4-(trifluoromethyl)cyclobutane, heptafluoro-(trifluoromethyl)cyclobutane and chloroheptafluorocyclobutane from a mixture comprising (a) said at least one perhalocycloalkane, (b) olefinic impurity, and (c) saturated fluorine-containing impurity selected from the group consisting of hydrochlorofluorocarbons, hydrofluorocarbons and mixtures thereof, comprising:
   (1) contacting the mixture with chlorine under conditions suitable for chlorinating the olefinic impurity and the saturated fluorine-containing impurity, thereby converting the olefinic impurity to a saturated impurity containing at least one chlorine substituent and reducing the hydrogen content of the saturated fluorine-containing impurity; and
   (2) separating said at least one perhalocycloalkane from the saturated chlorine-containing impurity produced from the olefinic impurity in (1) and the hydrogen-depleted saturated fluorine-containing impurity produced in (1).

6. A process for producing n-decafluorobutane comprising:
   contacting a mixture comprising octafluorocyclobutane and 1,1,1,2,3,4,4,4-octafluorobutene-2 with chlorine under conditions suitable for converting the 1,1,1,2,3,4,4,4-octafluorobutene-2 to 2,3-dichloro-1,1,1,2,3,4,4,4-octafluorobutane; separating the octafluorocyclobutane from the 2,3-dichloro-1,1,1,2,3,4,4,4-octafluorobutane; and reacting 2,3-dichloro-1,1,1,2,3,4,4,4-octafluorobutane with HF.

7. The process of claim 5 wherein the saturated fluorine-containing impurity is $C_2HClF_4$.

* * * * *